United States Patent [19]

Peterson et al.

[11] 4,320,661
[45] Mar. 23, 1982

[54] ELECTROMAGNETIC ACOUSTIC TRANSDUCER FOR TUBE INSPECTION

[75] Inventors: William E. Peterson; Robert B. Thompson, both of Thousand Oaks, Calif.; Carmine F. Vasile, Lloyd Neck, N.Y.

[73] Assignee: Electric Power Research Institute, Inc., Palo Alto, Calif.

[21] Appl. No.: 86,512

[22] Filed: Oct. 19, 1979

[51] Int. Cl.³ ............................................. G01N 29/04
[52] U.S. Cl. ..................................................... 73/643
[58] Field of Search .................. 73/643, 623, 637, 638

[56] References Cited

U.S. PATENT DOCUMENTS

| | | | |
|---|---|---|---|
| 3,600,613 | 8/1971 | Clarke | 73/637 |
| 3,850,028 | 11/1974 | Thompson et al. | 73/643 |
| 4,092,868 | 6/1978 | Thompson et al. | 73/643 |
| 4,127,035 | 11/1978 | Vasile | 73/643 |

*Primary Examiner*—Stephen A. Kreitman
*Attorney, Agent, or Firm*—Flehr, Hohbach, Test

[57] ABSTRACT

An electromagnetic transducer for exciting selected modes of ultrasonic vibration in a tubular body. The transducer includes a plurality of rows of permanent magnets of alternating polarity with a coil provided about the magnets whereby a current is conducted through the magnetic fields. The rows of magnets are provided in carriers which are yieldably biased towards the inner surface of a tubular body during inspection.

5 Claims, 8 Drawing Figures

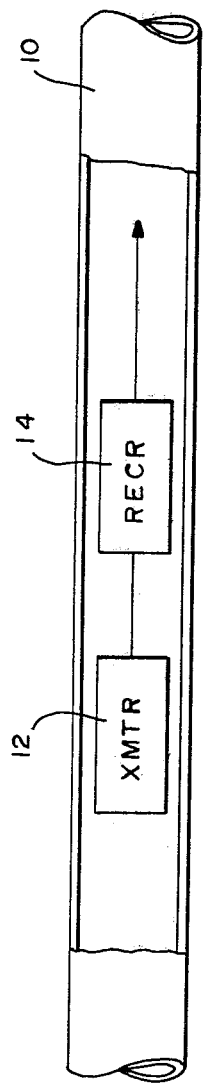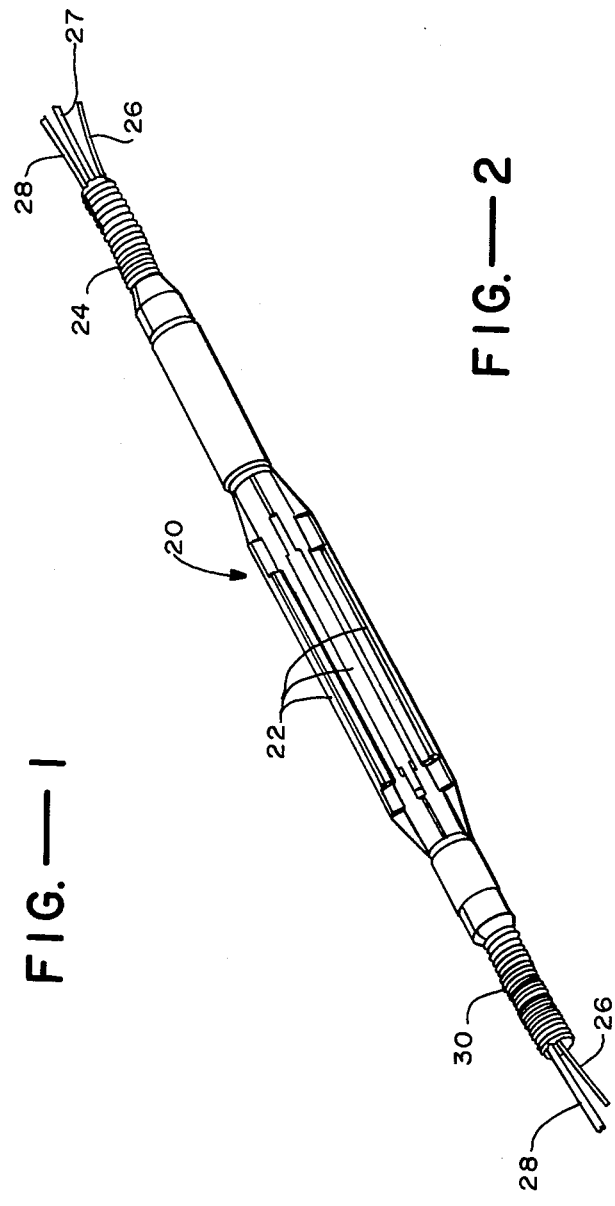

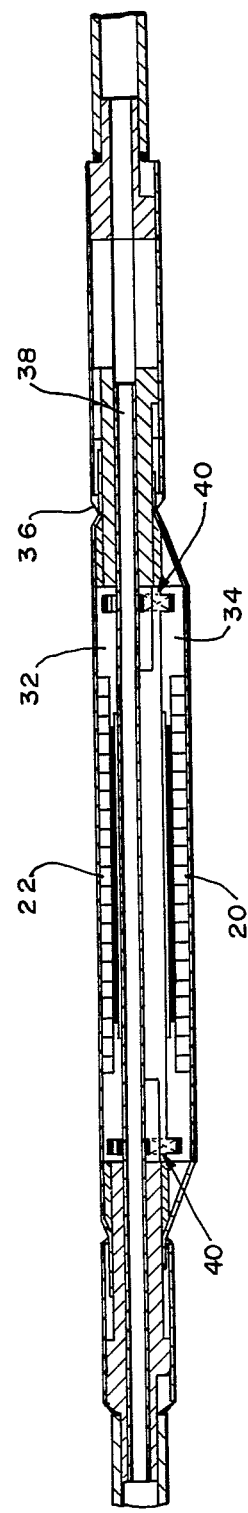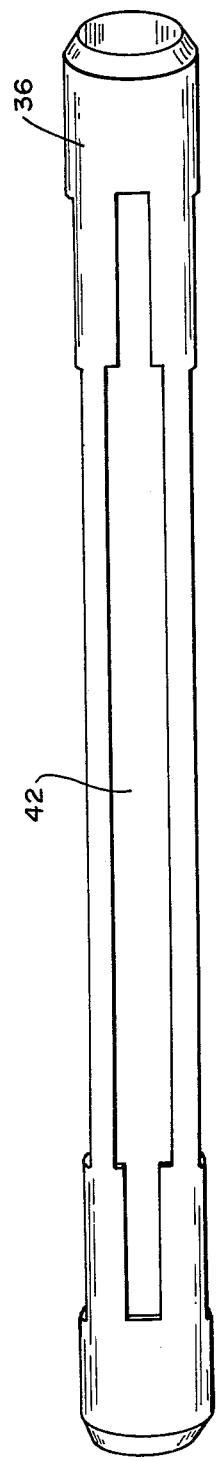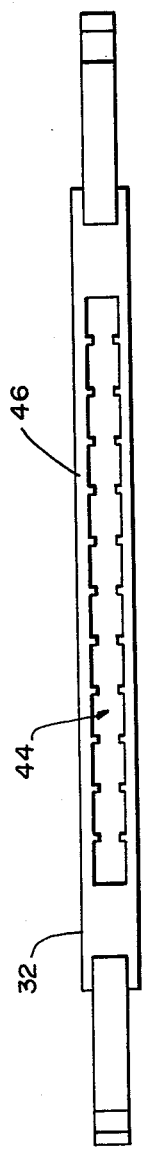
FIG.—3  FIG.—4  FIG.—5

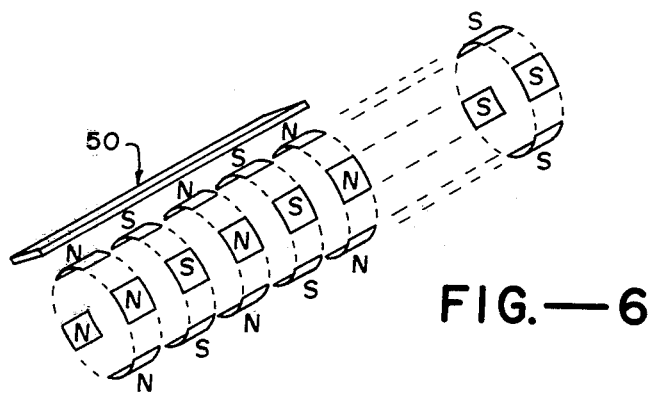
FIG.—6
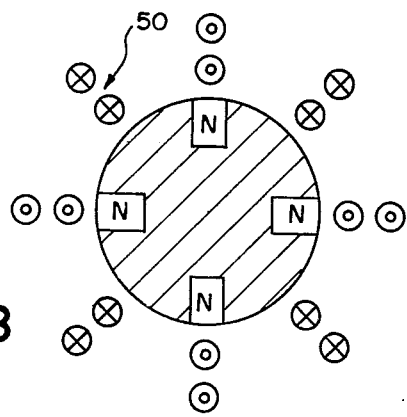
FIG.—8
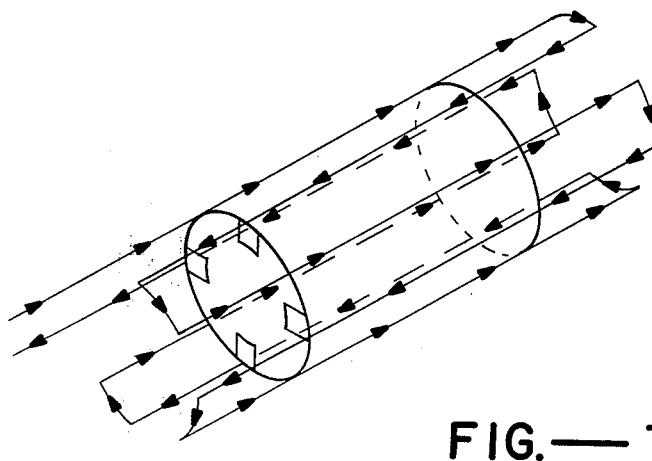
FIG.—7

ELECTROMAGNETIC ACOUSTIC TRANSDUCER FOR TUBE INSPECTION

This invention relates generally to transducers such as used in ultrasonic inspection systems, and more particularly the invention relates to an ultrasonic transducer for use in non-destructive inspection of tubular devices.

The invention of steam and water transmission tubes in boiling and pressurized water power generation equipment is essential to ensure safe and dependable operation of such power systems. A number of non-destructive techniques are known for inspecting the transmission tubes for such flaws as cracks, dents, and pits which could cause constructural failure under prolonged operating loads.

In ultrasonic test systems a wave is introduced into the inspected structure, and reflected waves from structural flaws are detected. Through analysis of reflected waves the size and location of defects can be determined.

U.S. Pat. No. 4,127,035 discloses an electromagnetic transducer for imparting and receiving ultrasonic waves. The transducer includes a row of permanent magnets for establishing a periodic magnetic field adjacent to a conductive material, and a coil is placed in the periodic magnetic field whereby current flowing through the coil establishes an elastic ultrasonic wave in the conductive material.

However, ultrasonic inspection of tubular structures is compounded because a plurality of modes, both radial and circumferential, can be simultaneously excited, and reflected signals from the plurality of modes can interfere and modulate signals reflected from a flaw, thereby increasing the difficulty of analyzing signals for flaw detection.

Accordingly, an object of the present invention is an improved transducer for use in ultrasonic inspection of tubular products.

Another object of the invention is an ultrasonic transducer which can excite selected modes in tubular bodies.

A feature of the invention is the provision of a plurality of equally spaced wave inducing segments or wave receiving segments in the transducer, where each segment includes means for establishing a periodic magnetic field and means for conducting a current in a direction through the magnetic field.

Briefly, in accordance with the invention a transducer for use in ultrasonic testing of a tubular body comprises a plurality of means for establishing periodic magnetic fields equally spaced about the inner surface of the tubular body. Means for conducting a current in substantially the same direction through the magnetic fields is provided whereby selected modes of vibration are established in the tubular body. Preferably, each of the plurality of means comprises a row of permanent magnets of alternating polarity, and the means for conducting a current comprises a coil positioned about the plurality of magnets. Advantageously, the coil may comprise a double sided printed circuit board.

The plurality of rows of magnets are supported in a plurality of carriers which is mounted on a support for movement through the tubular body. Preferably, means is provided for yieldably biasing the carriers toward engagement with the interior surface of the tubular body whereby the carrier and row of magnets can move over irregularities in the interior surface of the tubular body.

The invention and objects and features thereof will be more readily understood from the following detailed description and appended claims when taken with the drawing, in which:

FIG. 1 is a section view of a portion of a tube with ultrasonic inspection apparatus therein including electromagnetic transducers in accordance with the present invention.

FIG. 2 is a perspective view of one embodiment of an electromagnetic transducer in accordance with the present invention.

FIG. 3 is a side view in section of the transducer of FIG. 2.

FIG. 4 is a top view of a body portion of the transducer of FIG. 2.

FIG. 5 is a plan view of a magnet carrying the transducer of FIG. 2.

FIG. 6 is a perspective illustration of the magnets and coils in the transducer of FIG. 3.

FIG. 7 is a schematic of current flow in the coils of FIG. 6.

FIG. 8 is an end view of the magnets of FIG. 6 illustrating current flow.

Referring now to the drawings, FIG. 1 is a side view in section of a portion of a metal tube 10 with ultrasonic inspection apparatus therein. The inspection apparatus includes an ultrasonic transmitter 12 and an ultrasonic wave receiver 14 which are pulled through the tube 10 for inspection of the length of tube. Operation of such apparatus for ultrasonically testing a body for defects is disclosed in copending application Ser. No. A-35186 wherein a plurality of reflected waves are summed to enhance the signal to noise ratio of the signals and facilitate the analysis of the signals and detection of defects in the tube.

As noted above, a plurality of modes of ultrasonic vibration are possible in a tube, and if a number of modes of vibration are present the received signals are more difficult to coherently add for signal enhancement. In accordance with the present invention a transducer is provided which suppresses unwanted modes of vibration in a structure such as a tube. FIG. 2 is a perspective view of one embodiment of such a transducer shown generally at 20 which includes a plurality of rows 22 of magnets of alternating polarity for establishing a periodic magnetic field in the inner surface of the tubular body. The transducer probe 20 is attached by suitable coupler 24 to a nylon tubing (not shown) containing coaxial cables 26 and 28 through which electrical signals are transmitted from the transducer to external equipment. A similar coupler 30 is provided at the opposite end of the probe 20 for coupling to the transmitter 12 of FIG. 1. The rows of magnets are equally spaced around the perimeter of the probe. For example, four rows of magnets are spaced at 90° intervals.

FIG. 3 is a side view in section of probe 20 of FIG. 2 in which the top row of magnets 22 are supported in a carrier 32 and the bottom row of magnets 22 are supported in a carrier 34. The carriers 32 and 34 are positioned in an outer probe body 36 with the magnet carriers 32 and 34 yieldably biased away from a central support rod 38 by means of magnets 40. The top carrier 32 is shown in a retracted position with the carrier abutting the central rod 38 while carrier 34 is biased in its maximum extended position away from rod 38 by the opposing field of magnets 40. The outward travel of carriers 32 and 34 can be limited by the outer probe body 36 or by suitable mechanical stops, however such limited travel is not essential to the invention. By yieldably biasing the carriers, the transducer can move through a tube having variations in inner diameter due to such defects as dents.

Referring to FIG. 4, a top view of the outer probe body 36 is illustrated. The body is cylindrically shaped with a plurality of windows through which the carriers 32, etc. extend. For example, window 42 is provided through which one carrier, including a row of magnets projects. End portions of body 36 receive the coupler shown in FIGS. 2 and 3 for joining the outer housing with the main probe body.

FIG. 5 is a top view of a magnetic carrier 32 and includes a central cavity shown generally at 44 for receiving a plurality of rectangularly shaped magnets. In this embodiment twelve such magnets will be accommodated with the magnets epoxied into carrier 32 and of suitable dimension for extending with carrier 32 through window 42 of the outer probe body 36 shown in FIG. 4.

FIG. 6 is a perspective view illustrating the arrangement of the rows of magnets in the probe. The electrical coil associated with the row of magnets is provided by means of a thin double layers printed circuit board 50 which is attached to the outer surfaces of the magnets by suitable electrical insulative adhesive. Similar printed circuit board strips are provided adjacent to the surfaces of each of the other rows of magnets and between the rows of magnets to provide a coil arrangement as shown schematically in FIG. 7. Thus, it will be noted that the rows of magnets are arranged with parallel north and south polarities.

Accordingly, the current flow in the coil is in the same relative direction with respect to each row of magnets. In an alternative embodiment, the polarity of the magnets in adjacent rows can be opposite in which case the direction of current flow relative to each adjacent row of magnets will be in opposite directions.

FIG. 8 is an end view of the magnets of FIG. 6 illustrating the direction of current flow with a dot symbol representing current flow out of the plane of the drawing and a cross symbol representing current flow into the plane of the drawing. As above noted and as illustrated, the coil comprises two turns provided by the double layer printed circuit board.

In the illustrated embodiment the probe consists of four segments or rows of magnets arranged in equal intervals around the tube. In this embodiment every fourth mode would be excited with other modes being suppressed. An individual mode can then be excited by appropriate choice of drive frequency. It will be appreciated that by providing a different number of magnet segments other modes can be excited, if desired.

Thus, while the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A transducer for use in ultrasonic testing of a tubular product comprising
   a plurality of means for establishing periodic magnetic fields equally spaced about the inner surface of a tubular body, each of said means comprising a row of permanent magnets of alternating polarity and alignable parallel to the axis of said tubular product, said plurality of means being equally spaced about the circumference of said inner surface, and
   means for conducting a current through said magnetic fields whereby selected modes of vibration are established in said tubular body.

2. A transducer as defined by claim 1 wherein said means for conducting a current comprises a coil positioned about said means for establishing periodic magnetic fields.

3. A transducer as defined by claim 2 wherein said coil comprises a double sided printed circuit board.

4. A transducer as defined by claim 1 and further including a plurality of carriers for said plurality of rows of magnets, and a support means for supporting said carriers.

5. A transducer as defined by claim 4 and further including means for yieldably biasing said carriers and rows of magnets towards the interior surface of a tubular body during inspection.

* * * * *